(12) United States Patent
Takagi et al.

(10) Patent No.: US 8,283,154 B2
(45) Date of Patent: Oct. 9, 2012

(54) METHOD OF DECONTAMINATING POLLUTED ENVIRONMENTS WITH BACTERIA ON A POROUS SUPPORT

(75) Inventors: Kazuhiro Takagi, Ibaraki (JP); Naoki Harada, Ibaraki (JP); Yuuichi Yoshioka, Kochi (JP)

(73) Assignees: National Institute for Agro-Environmental Sciences Independent Administrative Institute, Ibaraki (JP); Kazuhiro Takagi, Ibaraki (JP); Kowa Co., Ltd., Aichi (JP)

( * ) Notice: Subject to any disclaimer, the term of this patent is extended or adjusted under 35 U.S.C. 154(b) by 473 days.

(21) Appl. No.: 12/561,078

(22) Filed: Sep. 16, 2009

(65) Prior Publication Data

US 2010/0006499 A1 Jan. 14, 2010

Related U.S. Application Data

(62) Division of application No. 11/335,686, filed on Jan. 20, 2006, now Pat. No. 7,629,159.

(30) Foreign Application Priority Data

Jan. 26, 2005 (JP) .................. 2005-108901
Jun. 9, 2005 (JP) .................. 2005-169369
Jun. 29, 2005 (JP) .................. 2005-189986

(51) Int. Cl.
 *A62D 3/02* (2007.01)
 *C12N 11/14* (2006.01)
 *C12N 11/02* (2006.01)
 *C12N 11/04* (2006.01)

(52) U.S. Cl. ............. 435/262.5; 435/176; 435/177; 435/182; 435/822; 435/830

(58) Field of Classification Search ............... None
 See application file for complete search history.

(56) References Cited

U.S. PATENT DOCUMENTS

| 6,451,580 B1 | 9/2002 | Takagi et al. |
| 6,498,028 B1 | 12/2002 | Takagi et al. |
| 6,569,333 B1 | 5/2003 | Takagi et al. |

FOREIGN PATENT DOCUMENTS

| JP | 10-225288 | 8/1998 |
| JP | 11-318435 | 11/1999 |
| JP | 3030370 | 2/2000 |
| JP | 2003-250529 | 9/2003 |
| JP | 2005-027536 | 2/2005 |
| WO | WO00/78923 | 12/2000 |

OTHER PUBLICATIONS

Iwasaki, A., et al., "In situ bioremediation of triazine herbicide contamination by bacterial consortium," Brain Techno News, Jan. 15, 2005, No. 107, pp. 31-35, National Agriculture and Bio-oriented Research Organization, Tokyo, Japan, with partial English translation.

"In situ bioremediation of pesticide contamination using charcoal material enriched with bacteria consortium," Agricultural Technology, Oct. 1, 2004, vol. 59, No. 10, pp. 449-454, Association for Advancement of Agricultural Science, Tokyo, Japan, with partial English translation.

Office Action from Japanese Patent App. No. 2005-189986 (Mar. 7, 2011).

*Primary Examiner* — David Naff

(74) *Attorney, Agent, or Firm* — Cermak Nakajima LLP; Tomoko Nakajima

(57) ABSTRACT

The present invention provides a stable complex microbial system, which simultaneously decomposes a plurality of organic contaminants even under a polluted environment with these contaminants and permits more effective decomposition of persistent organic contaminants such as PCNB and simazine. A support for holding a complexed accumulation of degrading bacteria, which contains a porous material provided as a support on which a degrading bacterium A capable of degrading at least one organic contaminant and a degrading bacterium B capable of degrading another organic contaminant are accumulated, is produced. The degrading bacterium A may be a PCNB-degrading bacterium, particularly a degrading bacterium containing a degrading bacterium having part or all of mycological characteristics of *Nocardioides* sp. PD653 and the degrading bacterium B may be a degrading bacterium containing a degrading bacterium having part or all of mycological characteristics of β-*Proteobacteria* CDB21.

12 Claims, 9 Drawing Sheets

LANE 1: CDB21+CSB1+CD7w+PD653
LANE 2: PD3+CD7 SURFACE DAY 0
LANE 3: PD3+CD7 SURFACE DAY 28
LANE 4: PD3+CD7 INSIDE   DAY 0
LANE 5: PD3+CD7 INSIDE   DAY 28
LANE 6: PD3+2Mix SURFACE DAY 0
LANE 7: PD3+2Mix SURFACE DAY 28
LANE 8: PD3+2Mix INSIDE   DAY 0
LANE 9: PD3+2Mix INSIDE   DAY 28

METHOD OF DECONTAMINATING POLLUTED ENVIRONMENTS WITH BACTERIA ON A POROUS SUPPORT

This application is a divisional claiming priority under 35 U.S.C. §120 to U.S. patent application Ser. No. 11/335,686, filed Jan. 20, 2006, now U.S. Pat. No. 7,629,159, which claims priority under 35 U.S.C. §119 to Japanese Patent Application No. 2005-018901, filed Jan. 26, 2005, Japanese Patent Application No. 2005-169369, filed Jun. 9, 2005, and Japanese Patent Application No. 2005-189986, filed Jun. 29, 2005, which are incorporated in their entireties by reference. The Sequence Listing in electronic format filed herewith is also hereby incorporated by reference in its entirety (File Name: 1002-0039DIV_Seq_List; File Size: 4 KB; Date Created: Sep. 16, 2009).

BACKGROUND OF THE INVENTION

1. Field of the Invention

The present invention relates to a technique for decomposing and removing organic contaminants contained in crop land soil, underground water, or the like. In particular, the present invention relates to a technique for decomposing and removing contaminants from soil, underground water, or the like, which has been contaminated by a plurality of organic contaminants, and to a technique for decomposing a persistent organic contaminant, by utilizing soil bacteria.

2. Description of the Related Art

In late years, a bio-remediation technique, which is able to decontaminate and safe the contaminated soil or the like by means of natural degrading abilities of microorganisms such as bacteria, has attracted attention as a technique for decomposing and removing persistent organic contaminants such as POPs in low concentration distributed widely in crop land soil, or the like. However, even though the conventional bio-remediation technique would utilize microorganisms such as bacteria effectively, the discovery of a degrading bacterium that decomposes an organic contaminant effectively has been difficult. Alternatively, even if the degrading bacterium can be discovered, the bacterium has its own living environment and the density of the degrading bacterium can be low in natural state, so a contaminant cannot be effectively prevented from remaining or scattering in the environment. In particular, in consideration of the application of the bio-remediation technique to contaminated soil or the like, problems have been risen such that the physical and chemical properties of contaminated soil affect the degrading bacteria and the degrading bacteria are extinct as a result of predation with protozoa in the contaminated soil. Therefore, even though there are increasing demands on the effective application of bio-remediation technique, in actual, such a technique has not been realized up to that required.

On the other hand, the inventors of the present invention have found that a porous material having a predetermined absorption constant or specific surface can be utilized as a degrading bacterial habitat for organic contaminants and have developed technique for accumulating and isolating a specific degrading bacterial species (Japanese Patent No. 3030370: Patent Document 1, Japanese Patent No. 2904432: Patent Document 2, and WO 00/078923: Patent Document 3). Those technologies have allowed any kind of organic contaminant which has been used in an agricultural chemical or the like and remained in environments, for example in soil, to be decomposed and removed by thickly accumulating and purifying degrading bacteria capable of decomposing the organic contaminant.

In many cases, two or more organic contaminants may cause environmental contamination such as soil and water contamination. However, there is no technique developed for simultaneously decomposing and removing those contaminants in place.

In addition, it is difficult to decompose organic contaminants which may be one of the causes of soil or water contamination, such as organochlorine pesticide PCNB (quintozene: pentachloronitrobenzene), which is hardly decomposed, and simazine (2-chloro-4,6-bis(ethylamino)-1,3,5-triazine), which has a long half-life and a low soil-adsorption coefficient. Therefore, novel technique for more effectively decomposing the organic contaminants has been demanded in the art.

SUMMARY OF THE INVENTION

The present invention, therefore, intends to obtain a complex microbial system having stability, even in an environment of being contaminated with plural organic contaminants, which is capable of simultaneously decomposing these contaminants.

In addition, the present invention intends to decompose a persistent organic contaminant, such as PCNB or simazine in particular, more effectively.

To achieve the objects, according to one aspect of the present invention, there is provided a support for holding a complexed accumulation of degrading bacteria, including: a porous material; a degrading bacterium A capable of degrading at least one organic contaminant, the degrading bacterium A being accumulated on the porous material; and a degrading bacterium B capable of degrading another organic contaminant, the degrading bacterium B being accumulated on the porous material.

A support for holding a complexed accumulation of degrading bacteria is obtained by accumulating a degrading bacterium A capable of decomposing at least one organic contaminant and a degrading bacterium B capable of decomposing another organic contaminant on a porous material, so that two or more organic contaminant can be decomposed and removed. Here, the "degrading bacterium A" and the "degrading bacterium B" refer to different degrading bacteria, respectively. Each of the degrading bacterium A capable of decomposing at least one organic contaminant and the degrading bacterium B capable of decomposing another organic contaminant may be a single degrading bacterium, or may be provided as a bacterial group consisting of a combination of one or more symbiotic bacteria. The support for holding a complexed accumulation of degrading bacteria is able to decompose an organic contaminant such as a triazine chemical or an organochlorine pesticide by being mixed in contaminated soil or being passed through contaminated water.

In addition, the degrading bacterium A may be a PCNB-degrading bacterium, while the degrading bacterium B may be a simazine-degrading bacterium. In this case, a support for holding a complexed accumulation of degrading bacteria, in which the accumulation is of at least one of the PCNB- and simazine-degrading bacteria or at least both of them in a porous material, can be obtained, thereby allowing PCNB or simazine or both of them to be decomposed from a processing object.

Furthermore, the degrading bacterium A may be any of degrading bacteria including bacteria having part or whole of mycological characteristics of *Nocardioides* sp. PD653 (hereinafter, simply referred to as "PD653"). In addition, the degrading bacterium B may be any of degrading bacteria including bacteria having part or whole of mycological characteristics of β-*Proteobacteria* CDB21. Consequently, a support for holding a complexed accumulation of degrading bacteria can be provided as one having at least one of *Nocardioides* sp. PD653 and β-*Proteobacteria* CDB21 or at least both of them accumulated in a porous material, thereby allowing PCNB or simazine or both of them to be decomposed from a processing object.

Here, the degrading bacterium A may be provided as a bacterial group obtained by combining with one or more symbiotic bacteria. Besides, the degrading bacterium B may be provided as a bacterial group obtained by combining with one or more symbiotic bacteria. In other words, each of the degrading bacteria A and B may be not only a single bacterium but also a bacterial group containing two or more different bacterial species. Furthermore, when the degrading bacterium A or B forms a complex microbial system (consortium) in combination with a symbiotic bacterium, it is not a simple combination of bacterial group but one having functions of complementing essential nutrient factors required for the decomposition and assimilation of an organic contaminant and for the growth of bacteria each other, thereby allowing an increase in degradation ability to the organic contaminant.

For instance, the degrading bacterium A may be a PCNB-degrading bacterium PD3 (hereinafter, abbreviated as "PD3") and the degrading bacterium B may be either of a simazine-degrading bacterium CD7 (hereinafter, abbreviated as "CD7") or a simazine-degrading bacterium 2Mix (hereinafter, abbreviated as "2Mix"). Here, the term "PD3" refers to a consortium containing *Nocardioides* sp. PD653, *Burkholderia cepacia* KTYY97 (hereinafter, abbreviated as "KTYY97"), and other bacterial species. In addition, the term "CD7" refers to a consortium containing β-*Proteobacteria* CDB21 (hereinafter, abbreviated as "CDB21"), *Bradyrhizobium japonicum* CSB1 (hereinafter, abbreviated as "CSB1"), and *Arthrobacter* sp. CD7w (hereinafter, abbreviated as "CD7w"). Here, the term "2Mix" refers to a consortium containing β-*Proteobacteria* CDB21 and *Bradyrhizobium japonicum* CSB1.

The porous material used in the present invention may be one having an adsorption constant several ten times or more and ten thousand times or less as great as the adsorption constant of soil where the degrading bacterium lives, or having a specific surface area of from 50 cm$^2$/g to 600 m$^2$/g (both inclusive). In other words, when the porous material has an adsorption constant several ten times or more and ten thousand times or less as great as the adsorption constant of soil where the degrading bacterium lives, or having a specific surface area of from 50 cm$^2$/g to 600 m$^2$/g (both inclusive), an assimilation material can be easily adsorbed in the form of which the degrading bacteria can be easily accessible and thus degrading bacteria can be stably accumulated on the support.

In addition, the porous material used in the present invention can be configured such that a volume ratio of pores having sizes that allow the fixation of a degrading bacterium to the whole of pores is 10% or more. When the porous material is one in which a volume ratio of pores having sizes that allow the fixation of a degrading bacterium to the whole of pores is 10% or more, the degrading bacterium can be easily propagated. Besides, the degrading bacterium can be stably grown. For satisfying such conditions, the pores having sizes ranging from 2 μm to 50 μm, preferably from 5 μm to 20 μm are preferably of 10% or more in volume ratio.

The porous material may be a carbonized ligneous material. When the porous material is the carbonized ligneous material, it is a suitable environment for the settlement of the degrading bacterium, thereby allowing the bacterium to be stably propagated and grown.

In addition, the present invention provides a bacterium that effectively decomposes an organochlorine pesticide PCNB. The bacterium may be a member of the genus *Nocardioides*, for example, *Nocardioides* sp. PD653 having a 16S rRNA (16s ribosomal RNA) containing a base sequence described in SEQ ID No: 1, which has been deposited as the Accession No. FERMP-20557 to the International Patent Organism Depositary, National Institute of Advanced Industrial Science, Japan, and a bacterium having part or all of the mycological characteristics of *Nocardioides* sp. PD653. Those bacteria are able to decompose PCNB completely in an effective manner.

Furthermore, the present invention provides a bacterium that lives in a symbiotic relationship with β-*Proteobacteria* CDB21 (FERMP-19395) that effectively decomposes a triazine chemical, particularly simazine. In particular, the bacterium is one grouped in *Arthrobacter*, such as *Arthrobacter* sp. CD7w deposited as the Accession No. FERMP-20371 at the International Patent Organism Depositary, National Institute of Advanced Industrial Science, Japan, and a bacterium having part or whole of mycological characteristics of *Arthrobacter* sp. CD7w. The bacterium, which contributes to an improvement in degradation ability to simazine, has a 16S rRNA gene that contains a base sequence described in SEQ ID No: 2. Any of those bacteria may act as a consortium by symbiotically living with a simazine-degrading bacterium (e.g., β-*Proteobacteria* CDB21) or the like to increase its affinity to the porous material. Therefore, the accumulation of simazine-degrading bacterial group on the porous material can be enhanced, thereby allowing higher degradation ability for triazine chemicals, particularly simazine, compared with the case in which only β-*Proteobacteria* CDB21 is present.

According to another aspect of the present invention, there is provided a method of producing a support for holding a completed accumulation of degrading bacteria, including the steps of: inoculating both a degrading bacterium A capable of degrading one organic contaminant and a degrading bacterium B capable of degrading another organic contaminant upon a porous material layer composed of laminated porous materials; and adding each of an inorganic salt medium A, which uses only the one organic contaminant as carbon and nitrogen sources, and an inorganic salt medium B, which uses only the other organic contaminant as carbon and nitrogen sources to the porous material layer after adjusting the concentration of each organic contaminant in the corresponding inorganic salt medium in proportion to an accumulation rate of each of the degrading bacteria A and B in the porous material when the inorganic salt media are added to the porous material layer, in which the degrading bacterium A and the degrading bacterium B are accumulated and held on the porous material.

The method is designed to include the steps of: inoculating both a degrading bacterium A capable of decomposing one organic contaminant and a degrading bacterium B capable of decomposing another organic contaminant upon a porous material layer composed of laminated porous materials; and, when an inorganic salt medium A, which uses only the one organic contaminant as carbon and nitrogen sources, and an inorganic salt medium B, which uses only the another organic contaminant as carbon and nitrogen sources, are added to the porous material layer, adding the inorganic salt media to the porous material after adjusting the concentration of each organic contaminant in the corresponding inorganic salt medium in proportion to the accumulation rate of the corresponding degrading bacterium A or B in the porous material. Therefore, the desired amounts of the degrading bacteria A and B can be held in the porous material even when the growth rates of the degrading bacteria A and B are different from each other.

More specifically, the method of producing a support for holding a complexed accumulation of degrading bacteria may be one in which the step of adding each of the inorganic salt media to the porous material layer after adjusting the concentration of each organic contaminant in the corresponding inorganic salt medium in proportion to an accumulation rate of each of the degrading bacteria A and B in the porous material further includes sub-steps of: adding one of the inorganic salt media A and B to the porous material layer at once; and adding the other of the inorganic salt media A and B to the porous material layer under reflux.

In the step of adding each of the inorganic media after adjusting the concentration of the organic contaminant in each of the inorganic salt media in proportion to an accumulation rate of each of the degrading bacteria A and B in the porous material, one of the inorganic media A and B is added to the porous material layer at once, and the other of the inorganic media A and B is added to the porous material layer under reflux. Therefore, for example, the inorganic salt medium B to be provided as an assimilation material for the degrading bacterium B having a higher growth rate is supplied through a reflux solution. On the other hand, at the beginning, the inorganic salt medium A to be provided as an assimilation material for the degrading bacterium A having a lower growth rate is added all at once to the porous material. Thus, the degrading bacterium having a lower growth rate can be sufficiently propagated and grown without the occupation of niche (the habitat of degrading bacterium) by the degrading bacterium having a higher growth rate alone. Therefore, a support for holding a completed accumulation of degrading bacteria, in which the degrading bacteria A and B live symbiotically together, can be obtained. Here, the term "growth rate" means the rate of growth or multiplication of a bacterial group in the porous material.

Furthermore, the degrading bacterium A may be a PCNB-degrading bacterium and also the degrading bacterium B may be a simazine-degrading bacterium. In this case, therefore, a support for holding a completed accumulation of degrading bacteria, in which the desired amounts of the PCNB-degrading bacterium and the simazine-degrading bacterium are held in the porous material, can be obtained.

Furthermore, the method of manufacturing a support for holding a complexed accumulation of degrading bacteria may be one in which the degrading bacterium A is a degrading bacterium containing a degrading bacterium having part or all of mycological characteristics of *Nocardioides* sp. PD653 and the degrading bacterium B is a degrading bacterium containing a degrading bacterium having part or all of mycological characteristics of β-*Proteobacteria* CDB21. In this cases, therefore, a support for holding a complexed accumulation of degrading bacteria, in which the required amounts of the bacterium having part or all of mycological characteristics of *Nocardioides* sp. PD653 and the bacterium having part or all of mycological characteristics of β-*Proteobacteria* CDB21 are held in the porous material, can be obtained.

Here, each of the degrading bacterium A and the degrading bacterium B may be a single degrading bacterium or may be combined with one or more symbiotic bacteria to form a bacterial group. When a consortium is formed by making a combination with one or more symbiotic bacteria, the consortium is not a simple combination of bacterial group but one having functions of complementing essential nutrient factors required for the decomposition and assimilation of an organic contaminant and for the growth of bacteria each other. In this case, therefore, a support for holding a complexed accumulation of degrading bacteria having increased degradation ability to the organic contaminant can be obtained.

Concretely, for example, the PCNB-degrading bacterium may be a PCNB-degrading bacterium PD3 consisting of *Nocardioides* sp. PD653 and a symbiotic bacterium thereof, *Burkholderia cepacia* KTYV97, and other bacterial groups. In addition, the simazine-degrading bacterium may be: a simazine-degrading bacterium CD7 which is a bacterial group containing three species, β-*Proteobacteria* CDB21, a symbiotic bacterium thereof (*Bradyrhizobium japonicum* CSB1), and *Arthrobacter* sp. CD7w; or a simazine-degrading bacterium 2Mix in which the simazine-degrading bacterium contains β-*Proteobacteria* CDB21 and a symbiotic bacterium thereof (*Bradyrhizobium japonicum* CSB1).

According to another aspect of the present invention, there is provided a method of decontaminating a polluted environment, including the step of using a support for holding a complexed accumulation of degrading bacteria including: a porous material; a degrading bacterium A capable of degrading at least one organic contaminant, the degrading bacterium A being accumulated on the porous material; and a degrading bacterium B capable of degrading another organic contaminant, the degrading bacterium B being accumulated on the porous material.

A support for holding a complexed accumulation of degrading bacteria, in which a bacterium A capable of degrading at least one organic contaminant and a bacterium B capable of degrading other organic contaminant are accumulated on a porous material, is used. Therefore, it becomes possible to decompose and remove at least two organic contaminants, thereby decontaminating a polluted environment.

The method of decontaminating a polluted environment can be designed such that the degrading bacterium A for decomposing one organic contaminant is a PCNB-degrading bacterium and the degrading bacterium B for decomposing the other organic contaminant is a simazine-degrading bacterium, or the degrading bacterium A is *Nocardioides* sp. PD653 or a bacterium having part or all of mycological characteristics of *Nocardioides* sp. PD653 and the degrading bacterium B is β-*Proteobacteria* CDB21 or a bacterium having part or all of mycological characteristics of β-*Proteobacteria* CDB21.

Furthermore, the method of decontaminating a polluted environment can be designed such that the degrading bacterium A is provided as a bacterial group obtained by making a combination with one or more symbiotic bacteria and the degrading bacterium B is provided as a bacterial group obtained by making a combination with one or more symbiotic bacteria. In other words, each of the degrading bacteria A and B can be provided as not only a single bacterial species but also a bacterial group containing a plurality of bacterial species. Besides, the method of decontaminating a polluted environment can be designed such that a complex microbial system (consortium) formed by combining the degrading bacterium A or B with its symbiotic bacterium is not a simple combination of bacterial group but one having functions of complementing essential nutrient factors required for the decomposition and assimilation of an organic contaminant and for the growth of bacteria each other, thereby allowing an increase in degradation ability to the organic contaminant.

PCNB and simazine, which are organic contaminants, can be decomposed when the degrading bacterium A is a PCNB-degrading bacterium and the degrading bacterium B is a simazine-degrading bacterium. In addition, when the degrading bacterium A is *Nocardioides* sp. PD653, a bacterium having part or all of mycological characteristics of *Nocardioides* sp. PD653, or a PCNB-degrading bacterium PD3, while the degrading bacterium B is β-*Proteobacteria* CDB21, a bacterium having part or all of mycological characteristics of β-*Proteobacteria* CDB21, or a simazine-degrading bacterium CD7 or 2Mix, each of PCNB and simazine can be almost completely (90% or more) decomposed. Likewise, organochlorine contaminants such as pentachlorophenol (PCP) and hexachlorobenzene (HCB) and triazine organic contaminants such as atrazine (2-chloro-4-ethylamino-6-isopropylamino-1,3,5-triazine) can be also decomposed.

According to another aspect of the present invention, there is provided a method of decontaminating a polluted environment, including: passing processing-object water through the support for holding a complexed accumulation of degrading bacteria; and degrading an organic contaminant in the processing-object water to decompose and remove the organic contaminant from the processing-object water.

The support for holding a complexed accumulation of degrading bacteria is designed such that processing-object water containing organic contaminants can pass through the support. Therefore, the organic contaminant in the processing-object water can be decomposed and removed by the degrading bacteria accumulated in the support for holding a complexed accumulation of degrading bacteria, thereby decontaminating the processing-object water. Therefore, the contaminated processing-object water can be decontaminated by carrying out only a simple process of passing the processing-object water through the support for holding a complexed accumulation of degrading bacteria.

According to another aspect of the present invention, there is provided a method of decontaminating a polluted environment, including mixing the support for holding a complexed accumulation of degrading bacteria in processing-object soil to decompose and remove an organic contaminant from the processing-object soil.

The support for holding a complexed accumulation of degrading bacteria is mixed in processing-object soil, so that organic contaminants contained in the soil can be transferred by rain water or the like to the support for holding a complexed accumulation of degrading bacteria and then decomposed. Therefore, by carrying out a simple processing of mixing the support for holding a complexed accumulation of degrading bacteria in the soil contaminated with organic contaminants by mixing the organic contaminants in the contaminated soil can be decomposed and removed to decontaminate the contaminated soil.

Furthermore, the present invention provides a device for decontaminating a support for holding a complexed accumulation of degrading bacteria. The device for decontaminating a polluted environment contains a support for holding a complexed accumulation of degrading bacteria, so that organic contaminants can be easily decomposed and removed, thereby decontaminating a polluted environment.

According to the support for holding a complexed accumulation of degrading bacteria of the present invention, a plurality of organic contaminants contained in the contaminated soil and underground water can be simultaneously decomposed and the degradation ability of the support can be sustained in a stable manner.

The bacteria of the present invention can contribute to the complete decomposition of persistent PCNB and simazine.

The method of manufacturing a support for holding a complexed accumulation of degrading bacteria of the present invention can simply produce a support for holding a complexed accumulation of degrading bacteria in which two or more degrading bacterial species capable of decomposing different organic contaminants are accumulated and held in a porous material.

According to the method and device of decontaminating a polluted environment of the present invention, the polluted environment can be decontaminated by simply decomposing and removing two or more organic contaminants without requiring a complicated processing process.

The above description of the present invention should not be construed restrictively; the objects, advantages, features, and uses of the present invention will become still more apparent from the following description given with reference to the accompanying drawings. Further, it should be understood that all appropriate modifications made without departing from the gist of the present invention are covered by the scope of the present invention.

DETAILED DESCRIPTION OF THE PREFERRED EMBODIMENT

Figure 1:
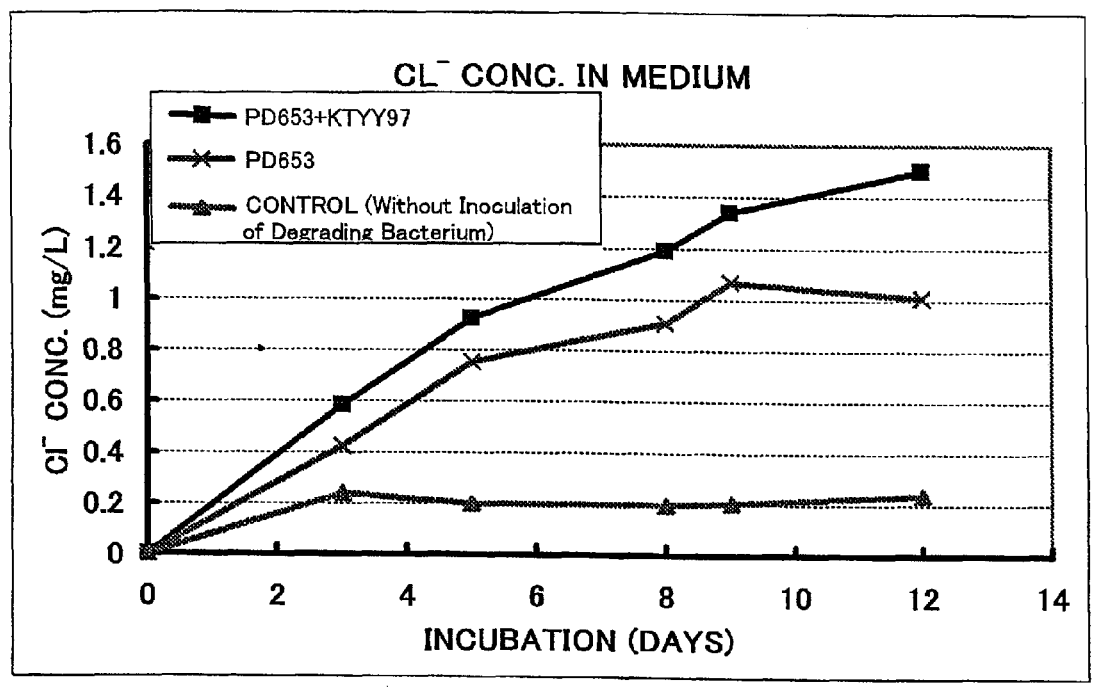
FIG. 1 is a graphical representation of the relationship between the number of incubation days for PCNB-degrading bacterium and the concentration of chloride ion.

Hereinafter, the support for holding a complexed accumulation of degrading bacteria and the bacteria of the present invention will be described in detail. The "support for holding a complexed accumulation of degrading bacteria" as used herein refers to accumulation of two or more degrading bacteria, which are capable of decomposing organic contaminants to be decomposed, at high density in a porous material.

Now, a support to be used in the support for holding a complexed accumulation of degrading bacteria and the degrading bacteria will be described below.

Support

The support for holding a complexed accumulation of degrading bacteria capable of decomposing organic contaminants may be a micro-habitat to be provided as a habitat of the degrading bacterium. The micro-habitat can be selected from porous materials each having many pores, a high adsorption coefficient, and a large effective surface area through which the degrading bacterium can be incorporated. That is, the specific surface is preferably from 50 $m^2/g$ to 600 $m^2/g$. In other words, the pore size is preferably from 2 μm to 50 μm, more preferably from 5 μm to 20 μm. Furthermore, it is preferable that such large-sized pores account for 10% or more of all of the pores in terms of volume percent. The porous material may be a carbonized ligneous material. For instance, a carbonized ligneous material A (5-mm to 10-mm chips of carbonized ligneous material obtained by subjecting broad leaved tree to general baking at 500° C., having a pH value of 8, a specific surface of 100 $m^2/g$, and the volumes of pores having diameters of 5 μm to 20 μm account for 10% or more of the total pore volume, as described in Japanese Patent No. 2904432) developed by the inventors of the present invention is an excellent micro-habitat. The carbonized ligneous material is preferably chipped into chips each having a size of about 2 mm to 15 mm. By the way, carbide such as activated carbon is not appropriate as a habitat of the degrading bacterium. Although such carbide can adsorb organic contaminants temporarily, the adsorption can be saturated immediately, thereby causing the need of replacing the carbide with new one. Therefore, the carbide is not sustainable to the stable use of extended period.

Degrading Bacteria

Degrading bacteria that decompose specific kinds of organic contaminants can be used. Those degrading bacteria used may be those having enhanced degradation ability obtained using a genetic recombinant technique or those newly created. However, regarding to the safety evaluation on release of recombinant microorganisms to the open-air, researches and discussions have been still continued and a public acceptance has been also difficult to be obtained.

On the other hand, it is preferable to use a degrading bacterium obtained by a soil reflux method which has been proposed by the inventors of the present invention because the degrading bacterium obtained by this method is one living in soil and having a negligibly small problem for safety. An improved soil reflux method forms an accumulation soil layer by mixing a porous material to be provided as a micro-habitat in soil where the degrading bacteria to be accumulated live and then refluxes an inorganic salt medium using only organic contaminants to be decomposed by the degrading bacteria as carbon and nitrogen sources for the predetermined number of days. Next, the micro-habitat is taken out from the accumulation soil layer and then inoculated on another micro-habitat prepared to prepare an accumulation layer constructed only of the micro-habitat. An inorganic salt medium using only organic contaminants to be decomposed by the degrading bacteria as carbon and nitrogen sources is refluxed again through the accumulation layer to accumulate the degrading bacteria of interest in a porous material. Alternatively, any degrading bacterium collected from soil by any other method may be used.

The isolation of degrading bacteria accumulated in the porous material on the basis of an improved soil reflux method can be carried out by a dilution plate technique or the like. For instance, the porous material with accumulated degrading bacteria is crushed and then suitably diluted with a phosphate buffer. Subsequently, the diluted solution is inoculated into an agar medium that contains a high concentration of a predetermined organic contaminant and then the whole is incubated. From a clear zone occurred in a plating medium, the bacterial cells are collected and then inoculated into a fresh agar medium, followed by incubation. In this way, a desired degrading bacterial colony is isolated.

A concrete example of the degrading bacterium includes the following degrading bacterium.

PCNB-degrading bacterium PD3: The PCNB-degrading bacterium PD3 is a bacterial group consisting of a complex system of *Nocardioides* sp. PD653, *Burkholderia cepacia* KTYY97, and other bacteria.

Isolation of PD653, KTYY97, and other bacterial groups from the PCNB-degrading bacterium PD3 is carried out such that the bacterium is inoculated from the colony of PD3 to a R2A agar plate containing PCNB to isolate a single colony and a part of the resulting colony is subjected to a tube culture to obtain a lineage. Finally, the resultant is incubated in a flask and then isolated therefrom.

*Nocardioides* sp. PD653 is a novel bacterium found by the inventors of the present invention and has been deposited as the Accession No. FERMP-20557 to the International Patent Organism Depositary (IPOD), National Institute of Technology and Evaluation (NITE), Tsukuba Central 6, 1-1-1, Higashi, Tsukuba, Ibaraki 305-8566, Japan on Jun. 8, 2005 as FERM P-20557. This deposit was converted to an International deposit under the Budapest Treaty on Aug. 22, 2005 as FERM BP-10405 *Nocardioides* sp. PD653 has degradation ability to PCNB and is grouped in the genus *Nocardioides* but not defined as a specific species.

PD653 has the following mycological characteristics. The incubation is carried out under the conditions of aerobic fermentation on a R2A agar medium at 30° C. for 3 to 7 days. The morphological characteristics include a colony having no spore formulation, 1.0 mm in diameter at 3 days of the incubation, pale yellow, circular form, swelling like a half-lens form, smoothened entire fringe, opaque, and butter-like consistency. Variations in colony morphology due to variation, and to incubation and physiological conditions are not recognized. The cell morphology is of *bacillus* having a size of about 0.7 to 0.8×1.0 to 1.2 μm without mobility and Gram-stained negative. Physiological characteristics are catalase: +, oxidase: −, acid/gas production (glucose): −/−, O/F test (glucose): −/−, and GC content: 70.8% (+: positive, −: negative).

On the basis of taxonomic characteristics with the phenotype of PD653 strain, the classification and identification thereof were carried out with reference to Bergey's Manual of Systematic Bacteriology, Vol. 1, N. R. Krieg, J. G. Holt (ed), Williams & Wilkins, Baltimore (1984). However, a short list of taxonomic groups having characteristic features analogous to those of PD653 could not be made.

Subsequently, as a result of molecular system analysis on the basis of a partial base sequence of 16S-rRNA of the PD653 strain of the present invention, when a homologous search to DNA data base (GeneBank/DDBJ/EMBL) is performed using FASTA and BLAST by determining continuous 1,487 bases in the base sequence of 16S-rRNA of PD653, the highest homology of 97.1% with *Nocardioides* sp. OS4 where the species has not been decided is shown. The results do not substantially conflict with the taxonomic characteristics of PD653 defined by its phenotype. Thus, PD653 is grouped in the genus *Nocardioides* sp. The above 1,487 bases are listed as SEQ ID NO: 1 in the sequence listing.

For investigating the degradation ability of PD653 to organic contaminants, PCNB having an initial concentration of 10 ppm was added to a medium containing 0.01% tripton and PD653 was then incubated at 30° C. in dark while shaking at 120 rpm, followed by determining the concentration of chlorine ions generated. As PCNB is decomposed, chlorine ions are generated, so the concentration of chlorine ions can be an indication of PCNB degradation. Incubation was carried out while shaking for 4 days under the conditions, whereby 4.5 ppm of chlorine ions generated. Incubation was carried out while shaking for 16 days under the same conditions, whereby 13.3 ppm of chlorine ions generated. In this way, PD653 had the degradation ability to PCNB alone. In addition, HCB having an initial concentration of 5 ppm is added instead of PCNB and then incubated 16 days while shaking under the same conditions, thereby generating 4.0 ppm of chlorine ions. From this, it is understood that PD653 had the degradation ability to HCB alone.

On the other hand, *Burkholderia cepacia* KTYY97 was deposited as FERMP-16809 and then transferred to the international deposit, followed by being deposited as FERMBP-6721 to the International Patent Organism Depositary, National Institute of Advanced Industrial Science, Japan. The details of the bacterium are described in Japanese Patent No. 2904432.

A PCNB-degrading bacterium PD3 forms a consortium by combining a plurality of bacteria such as PD653 and KTYY97. An acetone solution of PCNB at an initial concentration of 6 ppm is added to each of a support for holding a complexed accumulation of degrading bacteria in which PD653 and KTYY97 are accumulated in a porous material and a support for holding a complexed accumulation of degrading bacteria in which only PD653 is accumulated in a porous material and then incubated at 25° C. in dark while shaking at 120 rpm. Variation in chloride ion concentration per day is shown in FIG. 1. PD653 has the PCNB degrading ability. However, as is evident from FIG. 1, when PD653 is combined with at least KTYY97, an increased amount of PCNB can be decomposed.

Examples of symbiotic bacteria capable of constituting a consortium together with PD653 or the like having PCNB-degradation ability include *methylobacterium* sp. P4, *microbacterium* sp. P42, and *caulobacter* sp. P43 as well as KTYY97. The examples further include any bacterium other than those bacteria having abilities of assisting the growth of a degrading bacterium and accelerating the decomposition of PCNB.

PD653 and KTYY97, which constitute the above PCNB-degrading bacterium PD3, are accumulated and isolated using the improved soil reflux method. However, the present invention is not limited to them. PD653 is a bacterium grouped in the genus *Nocardioides*, which may be a bacterium having the ability of decomposing PCNB or a bacterium having part or all of the mycological characteristics of PD653. KTYY97 is a bacterium grouped in the genus *Burkholderia*, which may be a bacterium having part or all of the mycological characteristics of KTYY97.

Simazine-degrading bacteria CD7: Simazine-degrading bacteria (CD7) are a bacterial group, which consists of three kinds of strain, 13-*Proteobacteria* CDB21, *Bradyrhizobium japonicum* CSB1, and *Arthrobacter* sp. CD7w.

Isolation of CDB21, CSB1, and CD7w from the simazine-degrading bacterium CD7 is carried out such that the bacterium is inoculated from the colony of CD7 to a bactotrypsin agar plate containing simazine to isolate a single colony. CDB21, CSB1, and CD7w can be obtained as three colonies having different configurations.

β-*Proteobacteria* CDB21 is a novel bacterium discovered by the inventors of the present invention and is grouped in the genus β-*Proteobacteria*, but not in any species thereof known in the art. β-*Proteobacteria* CDB21 has been deposited as FERMP-19395 to the International Patent Organism Depositary, National Institute of Advanced Industrial Science and Technology, Japan. Only CDB21 possesses simazine-degradation ability of the simazine-degrading bacterium CD7.

*Bradyrhizobium japonicum* CSB1 belongs to a category of *Bradyrhizobium japonicum* and has been deposited as FERMP-19394 to the International Patent Organism Depositary, National Institute of Advanced Industrial Science and Technology, Japan.

*Arthrobacter* sp. CD7w is also a novel bacterium, which has been deposited as the Accession No. FERMP-20371 to the International Patent Organism Depositary, National Institute of Advanced Industrial Science, Japan.

CD7w has the following mycological characteristics. The incubation is carried out under the conditions of aerobic fermentation on a NA medium at 30° C. for 2 to 3 days. The morphological characteristics include a colony having no spore formation, 1 to 3 mm in diameter at 2 days of the incubation, pale yellow, circular form, swelling like a half-lens form, smoothened entire fringe, opaque, and butter-like consistency. Variations in colony morphology due to variation and to incubation and physiological conditions are not recognized. The cell morphology is of *bacillus* having a size of about 0.8×1.2 m with mobility and Gram-stained positive. Physiological characteristics are catalase: +, oxidase: –, O/F test: –, nitric acid reduction: –, pyrazinamidase: +, pyrrolidonyl allyl amidase: –, alkali phosphatase: –, β-glucuronidase: –, β-galactosidase: –, N-acetyl-β-glucosaminidase: –, esculin (glucosidase): +, urease: –, liquefaction of gelatin: +, fermentability of carbohydrate is glucose: –, ribose: –, xylose: –, mannitol: –, maltose: –, lactose: –, saccarose: +, and glycogen: –(+: positive, –: negative).

Classification and identification of CD7w on the basis of the taxonomic characteristic of CD7w's phenotype were performed, and the result decided that the CD7w was genus *Arthrobacter* in reference to Bergey's Manual of Systematic Bacteriology, Vol. I, N. R. Krieg, J. G. Holt (ed.), Williams & Wilkins, Baltimore (1984), and Bergey's Manual of Determinative Bacteriology (9th ed.), J. G. Holt, N. R. Krieg, P. H. A, Sneath, J. T. Staley, S. T. Williams (ed.), Williams & Wilkins, Baltimore (1994).

As a result of molecular system analysis on the basis of the base sequence of 16S-rRNA with respect to CD7w, continuous 831 bases in the base sequence of 16S-rRNA of CD7w were determined. When a homologous search to DNA data base (GeneBank/DDBJ/EMBL) is carried out using FASTA and BLAST, the highest homology of 99.9% with *Arthrobacter* sp. Ellin 146 where the species has not been decided is shown. Subsequently, CD7w is grouped into *Arthrobacter* sp. The above 831 bases are listed as SEQ ID NO: 2 in the sequence listing.

Any of CDB21, CSB1, and CD7w is hardly grown alone in an inorganic salt medium containing simazine as carbon and nitrogen sources, so that any distinct colony cannot be formed. Those combinations allow a colony to emerge when at least CDB21 and CSB1 are combined. Therefore, the simazine-degrading bacterium CD7 is not a simple combination of bacteria but forms a consortium having functions of complementing essential nutrient factors required for the decomposition and assimilation of simazine and for the growth of bacteria each other.

When the existence of the simazine-degrading bacterium CD7 in the porous material is investigated, among them, CD7w is scarcely present on the surface of the porous material but highly accumulated inside thereof. Therefore, in the consortium of CD7w, CDB21, and so on, the affinity to the porous material, which is insufficient only by CDB21 or the like, may have a function of accumulation in the porous material in a high density.

Mycobionts capable of constituting consortia together with CDB21 and the like having the ability for simazine-degrading include *Rhodococcus rhodochrous, Stenotrophomonas maltophilia, Nocardioides jensenii, Nocardioides fulvus, Nocardioides simplex*, and *Pseudomonas aeruginosa* as well as *Bradyrhizobium japonicum* such as CSB1 and *Arthrobacter* such as CD7w. Mycobionts capable of constituting consortia together with CDB21 and the like having the ability for simazine-degrading also include bacteria having an ability for support of degrading bacteria growth or enhancement of simazine-degrading except the bacteria described above.

CDB21, CSB1, and CD7w, which constitute the above simazine-degrading bacterium CD7, are those accumulated and isolated using an improved soil reflux method but the present invention is not limited thereto. Alternatively, CDB21 is a bacterium grouped in β-*Proteobacteria* having simazine-degradation ability, which may be a bacterium having part or all of the mycological characteristics of CDB21. In addition, CSB1 is a bacterium grouped in *Bradyrhizobium japonicum*, which may be a bacterium having part or all of the mycological characteristics of CSB1. Furthermore, CD7w may be a bacterium grouped in *Arthrobacter* having ability to assist the degradation of simazine and the growth of a symbiotic bacterium or may be a bacterium having part or all of the mycological characteristics of CD7w.

Simazine-degrading bacterium 2Mix: A simazine-degrading bacterium 2Mix is a bacterial group consisting of a complex of two species, β-*Proteobacteria* CDB21 and *Bradyrhizobium japonicum* CSB1, and is a simazine-degrading bacterium CD7 with a lack of CD7w. In other words, the simazine-degrading bacterium 2Mix has simazine-degrading ability in spite of lacking CD7w and exerts its functions as the simazine-degrading bacterium.

Method of Manufacturing a Support for Holding a Complexed Accumulation of Degrading Bacteria:

Next, the method of manufacturing a support for holding a complexed accumulation of degrading bacteria of the present invention, where the porous material and the degrading bacterium described above are used, will be described. For instance, on a sintered glass filter 2 placed in a reflux device 1, a porous material 3 to be provided as a micro-habitat is filled and subjected to a sterilization process in advance. To the porous material 3, only an organic contaminant, which is provided as an assimilation material of a degrading bacterium having a lower growth rate among the degrading bacteria to be accumulated, is dissolved and added. Next, one degrading bacterium and another degrading bacterium to be accumulated are inoculated to the porous material 3. After that, an inorganic salt medium 4 is refluxed for a suitable time period. Here, the inorganic salt medium utilizes only an organic contaminant to be provided as an assimilation material of a degrading bacterium having a rapid growth rate among the degrading bacteria to be accumulated as carbon and nitrogen sources. The reflux is carried out without drying the porous material 3 and without allowing the inorganic salt medium 4 to over flow from the porous material 3, thereby passing a constant amount of the inorganic salt medium 4 through the porous material 3. The reflux solution may preferably be replaced with new one about once per week. In addition, when the reflux solution is replaced, the organic contaminant to be provided as an assimilation material of the degrading bacterium having a lower growth rate is added to the porous material 3 in the same manner as one performed at the time of reflux. An objective support for holding a complexed accumulation of degrading bacteria can be obtained by repeating the addition and reflux of the organic contaminant. By the way, the method of manufacturing the support for holding a complexed accumulation of degrading bacteria is not limited to one using the device, and any device can be used as far as it can repeat the addition and reflux.

Method of Decontaminating Contaminated Environment:

For decontaminating an environment contaminated with an organic contaminant using a support for holding a complexed accumulation of degrading bacteria, the following usage can be given.

For the removal of an organic contaminant from contaminated soil, there is a usage in which the support for holding a complexed accumulation of degrading bacteria of the present invention is embedded in the contaminated soil and then mixed together. The organic contaminant which is already included in the soil may migrate (diffuse or transfer) together with rainwater or the like, followed by being adsorbed into the support for holding a complexed accumulation of degrading bacteria and decomposed by the degrading bacterium. Likewise, furthermore, an organic contaminant which can be newly dispersed or the like is also adsorbed in the support for holding a complexed accumulation of degrading bacteria and decomposed, thereby preventing the organic contaminant from remaining or dispersing in soil. According to this method, the contamination of an organic contaminant in soil into underground water can be prevented and underground water can be also prevented from contamination. As an application of this technique, an organic contaminant can be processed by mixing into: the surface layer and lower layer soil in which contaminants or the like can be present; the lower layer soil of a green surface of a golf course; the lower layer soil of an industrial waste processing facility; or the lower layer soil of a place for an organic waste solution.

In addition, if a carrier accumulation layer is formed such that the support for holding a complexed accumulation of degrading bacteria of the present invention is packed in a housing with air permeability, it can be provided as a simple bioreactor to serve as a device for decomposing and removing an organic contaminant. The device may be placed in a part of water conduit such as a domestic drainage canal, an agricultural drainage canal in a paddy field zone, or a drainage cannel in a golf course, thereby decomposing and removing an organic contaminant being dissolved and dispersed in water to decontaminate a polluted environment. In addition, in case of emergency, the support for holding a complexed accumulation of degrading bacteria of the present invention may be directly applied by dispersing on a contaminated area.

Examples

Hereinafter, the present invention will be described in further detail with respect to the following examples. However, the present invention is not limited to the examples.

Figure 2:
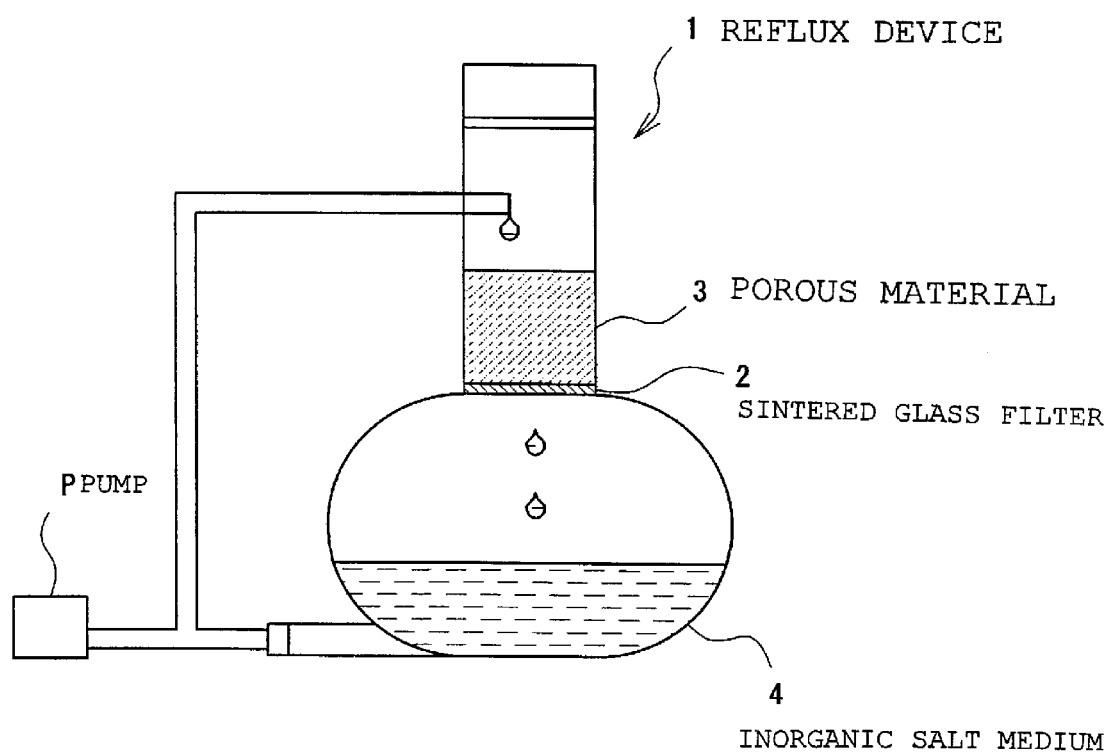
FIG. 2 is an external representation of a reflux device.
Figure 3:
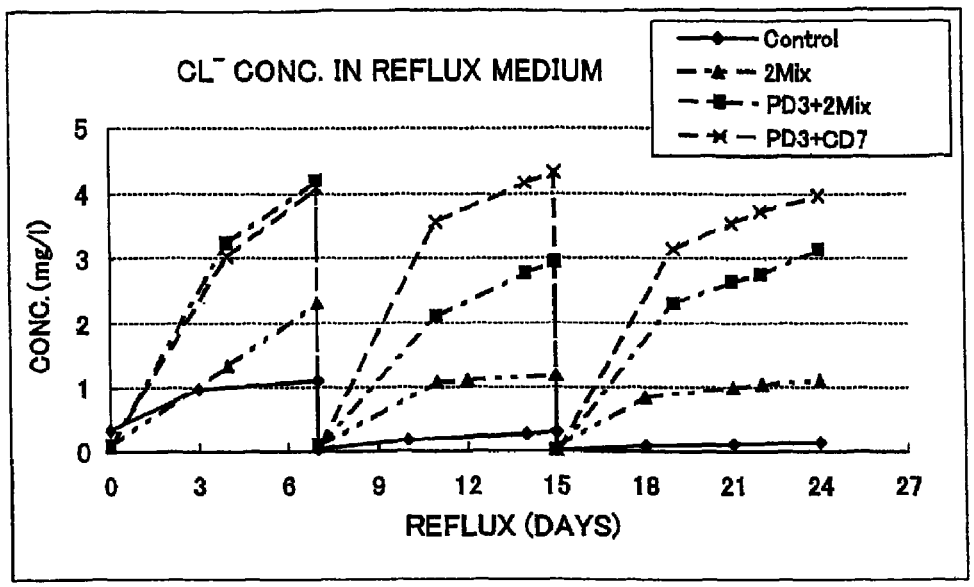
FIG. 3 is a graphical representation of the relationship between the number of reflux days and the concentration of chloride ion at the time of manufacturing a support for holding a complexed accumulation of degrading bacteria.
Figure 4:
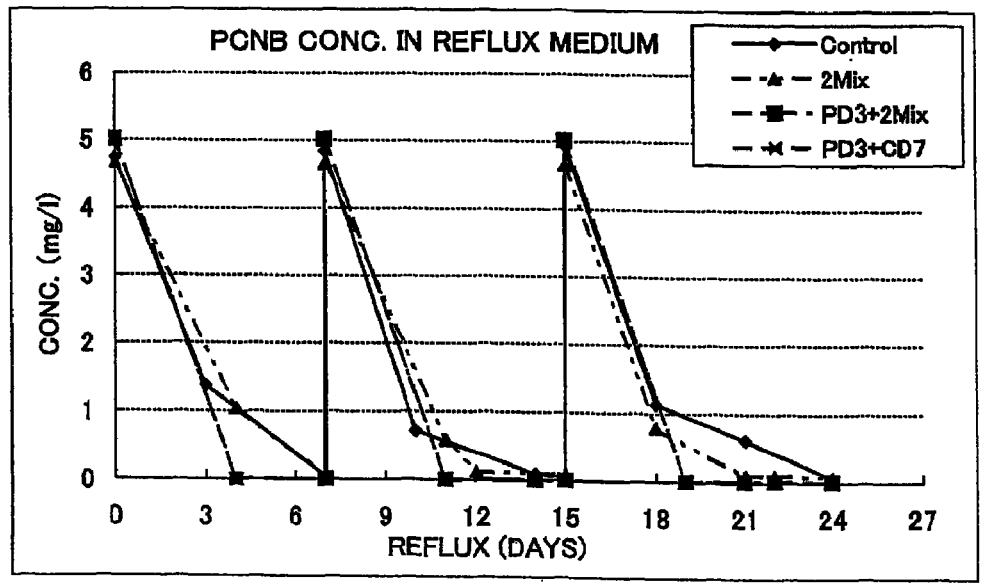
FIG. 4 is a graphical representation of the relationship between the number of reflux days and the concentration of PCNB at the time of manufacturing a support for holding a complexed accumulation of degrading bacteria.
Figure 5:
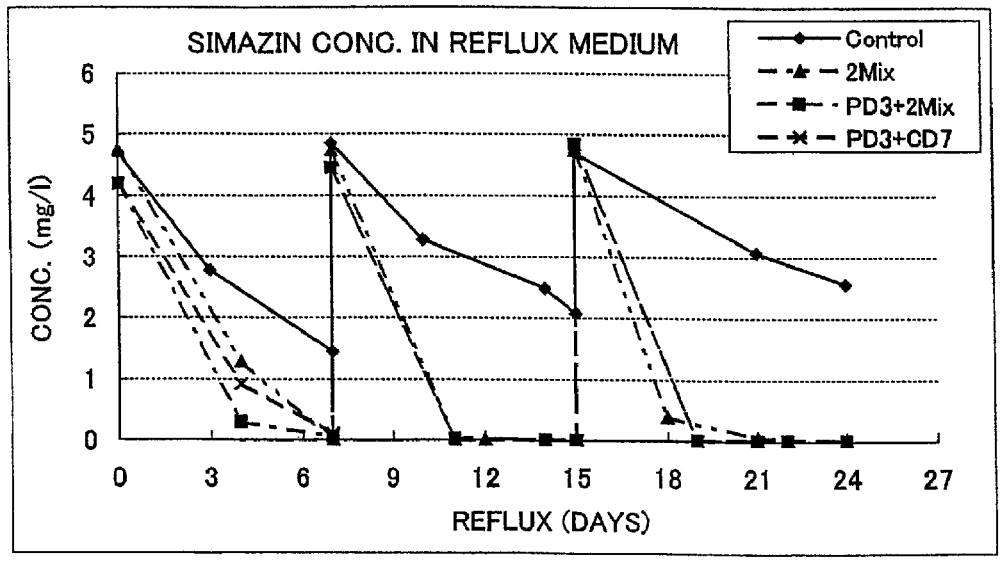
FIG. 5 is a graphical representation of the relationship between the number of reflux days and the concentration of simazine at the time of manufacturing a support for holding a complexed accumulation of degrading bacteria.

1. Method of Manufacturing a Support for Holding a Complexed Accumulation of Degrading Bacteria:

Support for holding a complex accumulation of degrading bacteria, on which RD3 and CD7 are held: A reflux device 1 shown in FIG. 2 was filled with about 7.5 g of a carbonized ligneous material A (5-mm to 10-mm chips of carbonized ligneous material obtained by subjecting broad leaved tree to general baking at 500° C., having a pH value of 8, a specific surface of 100 m$^2$/g, and the volumes of pores having diameters of 5 μm to 20 μm account for 10% or more of the total pore volume, as described in Japanese Patent No. 2904432) 3 to serve as a micro-habitat and then washed with ultrapure water, followed by subjecting to a sterilization process. The porous material 3 was added with 0.5 ml of a 3,000-ppm PCNB acetone solution and then inoculated with two colonies of each of PCNB-degrading bacterium PD3 and simazine-degrading bacterium CD7. Subsequently, 4,300 ml of a 5-ppm simazine inorganic salt medium (medium containing diammonium phosphate, dipotassium phosphate, monosodium phosphate, magnesium sulfate, and so on) was refluxed at 25° C. The reflux solution was replaced with new one once per week and at this time 0.5 ml of a 3,000-ppm PCNB acetone solution was newly added to the porous material 3. The reflux was carried out for three weeks. In this way, a support for holding a complexed accumulation of degrading bacteria of the present invention, in which the PCNB-degrading bacterium PD3 and the simazine-degrading bacterium CD7 were accumulated in the carbonized ligneous material A3, was obtained.

The total amount of PCNB to be provided as an assimilation material of the PCNB-degrading bacterium PD3, which was dissolved in acetone, was directly added to a porous material at first. On the other hand, simazine to be provided as an assimilation material of the simazine-degrading bacterium CD7 was added at a low concentration (5 ppm) to an inorganic salt medium, followed by refluxing. Therefore, the assimilation materials are added by different procedures, so that a support for holding a complexed accumulation of degrading bacteria, in which the required amounts of the PCNB-degrading bacterium PD3 and the simazine-degrading bacterium CD7 are retained in the carbonized ligneous material A can be obtained. However, if both PCNB and simazine are added at once to the porous material, the simazine-degrading bacterium CD7 having a higher growth rate occupies the porous material and most of the accumulation of the PCNB-degrading bacterium PD3 is not present. Simazine is dissolved in an inorganic salt medium and refluxed to control the rate of adsorption to the porous material, thereby lowering the accumulation rate of the simazine-degrading bacterium CD7.

Support for holding a complex accumulation of degrading bacteria, in which PD3 and 2Mix are held: The production of a support for holding a complexed accumulation of degrading bacteria was carried out such that a complex microbial system of the PCNB-degrading bacterium PD3 and the simazine-degrading bacterium 2Mix was constructed. A support for holding a complex accumulation of degrading bacteria, in which PD3 and 2Mix were held, was obtained by the same way as in the production of the support for holding a complex accumulation of degrading bacteria, in which PD3 and CD 7 were held, except that 2Mix was used instead of CD7.

Support for holding a complex accumulation of degrading bacteria, in which PD3, CD7, and 2Mix were held independently: A support for holding a complex accumulation of degrading bacteria, in which the CNB-degrading bacterium PD3, the simazine-degrading bacterium CD7, and the simazine-degrading bacterium 2Mix were independently accumulated (hereinafter, referred to as a "single fraction"), was produced. The production of a single fraction was also carried out by the same way as that of the support for holding a complex accumulation of degrading bacteria, PD3 and CD7. In this case, however, the degrading bacterium for an accumulation object to be inoculated in the porous material is two colonies, so that only the assimilation material of the target degrading bacterium can be provided. In other words, a 3,000-ppm PCNB acetone solution was not added before the reflux. For the production of the PCNB-degrading bacterium PD3, only 300 ml of a 5-ppm PCNB inorganic salt medium was refluxed. On the other hand, for the production of the simazine-degrading bacterium CD7 or 2Mix, only 300 ml of a 5-ppm simazine inorganic salt medium was refluxed to accumulate the degrading bacterium.

The resulting support for holding a complex accumulation of degrading bacteria was confirmed and evaluated as follows.

2. Confirmation of Accumulation Status of Degrading Bacterium into Porous Material [FIGS. 3 to 5]

For confirming the accumulation status of degrading bacterium in the porous material, the measurement of chlorine ion concentration as a decomposition product of PCNB or simazine was carried out from the initiation to termination of reflux. The chlorine ion concentration with respect to the number of reflux days is shown in FIG. 3. On the other hand, the measurement of PCNB and simazine concentrations was also carried out. The disappearance status of PCNB is shown in FIG. 4 and the disappearance status of simazine is shown in FIG. 5, respectively. The chlorine ion concentration obtained when PCNB and simazine are completely decomposed was 3.9 ppm. Thus, as shown in FIGS. 4 and 5, it is found that PCNB and simazine can be almost completely decomposed by carrying out reflux for 2 to 3 weeks. The growth environment of bacterium and the acquisition, conjugate metabolism, and co-localization of niche of the bacterium in competition with other bacteria are problems inherent to the bacterium. It is found that the PCNB-degrading bacterium PD3, and the simazine-degrading bacteria CD7 and 2Mix can be accumulated in sufficient amounts for decomposing PCNB and simazine. This can be proved from the disappearance status of PCNB or simazine.

3. Evaluation on the Number of Bacterial Cells of the Degrading Bacterium Accumulated in Porous Material [FIGS. 6 and 7]

The number of bacterial cells of the degrading bacterium accumulated in a support for holding a complexed accumulation of degrading bacteria was also evaluated. Evaluation on the number of bacterial cells of the degrading bacterium accumulated in a support for holding a complexed accumulation of degrading bacteria was carried out such that, after the reflux operation, 2 g of the porous material was taken off, added with 18 ml of a phosphate buffer, and then subjected to ultrasonication for 2 minutes. As a result, the degrading bacteria attached on the surface of the carbonized ligneous material A was removed from the carbonized ligneous material A and then the carbonized ligneous material A was taken from the buffer to obtain a "$10^1$-fold dilute solution". On the other hand, the removed carbonized ligneous material A was ground up into a pulverized product. Then, 1.0 g of the pulverized product was added with 9 ml of a phosphate buffer and the whole was shaken for 30 minutes, followed by ultrasonication for 1 minute to obtain a "$10^1$-fold dilute solution". Each of the $10^1$-fold dilute solutions was further serially diluted in an appropriate manner to obtain dilute solutions with five different dilution stages. A 1-ml aliquot was taken from each of the dilute solutions and then added to each of ten tubes in total where five tubes each contained 5 ppm of simazine inorganic salt medium and the other five tubes each contained 5 ppm of PCNB inorganic salt medium. Subsequently, those samples were incubated at 25° C. for 2 weeks and then the chlorine ion concentration of each sample was determined. Any sample having a chlorine ion concentration of 0.5 ppm or more was defined as "+". Besides, for each of the samples, the number of degrading bacterial cells on the surface of, or inside, the carbonized ligneous material A was determined using a MPN method.

Figure 6:
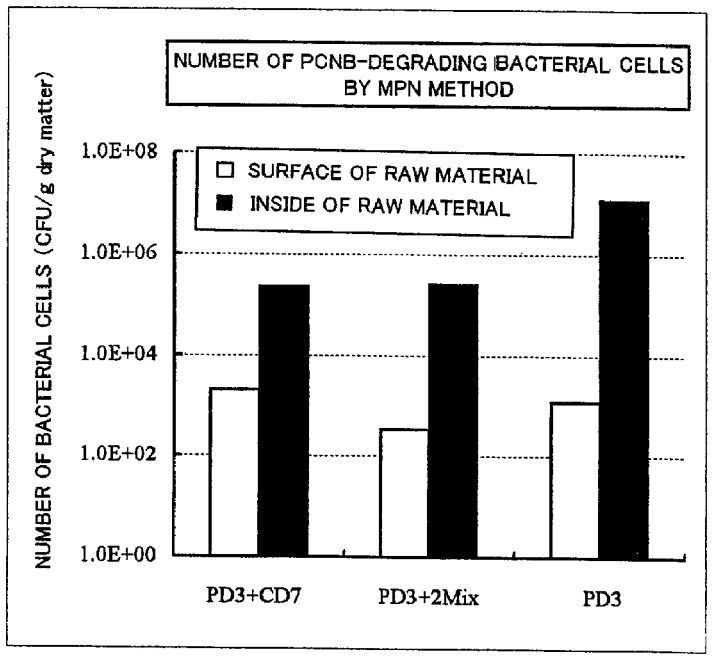
FIG. 6 is a graphical representation of the number of bacterial cells of the PCNB-degrading bacterium accumulated on the support for holding a complexed accumulation of degrading bacteria.
Figure 7:
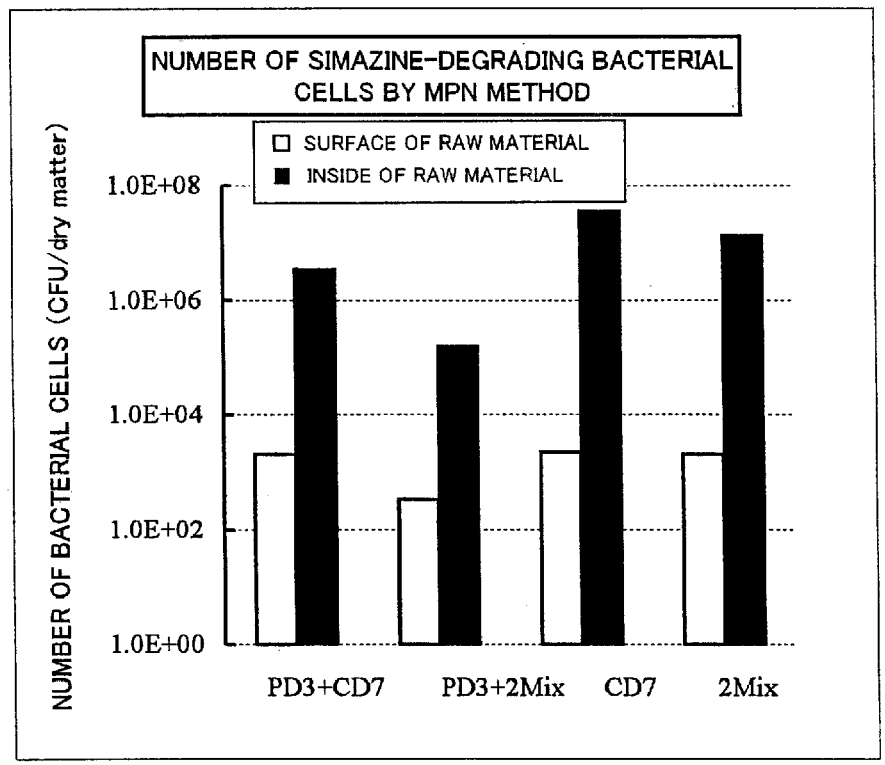
FIG. 7 is a graphical representation of the number of bacterial cells of the simazine-degrading bacterium accumulated on the support for holding a complexed accumulation of degrading bacteria.

The number of bacterial cells of the PCNB-degrading bacterium on the surface of, or inside, a support for holding a complexed accumulation of degrading bacteria, on which various kinds of degrading bacterium were held, is shown in FIG. 6 and the number of bacterial cells of the simazine-degrading bacterium is shown in FIG. 7. From the above measurement, it is found that the levels of the number of degrading bacterial cells are in the range of $10^4$ to $10^7$ CFU/g dried product. In addition, for each degrading bacterium, it is found that the bacterial cells are accumulated on the surface of the porous material (raw material surface) at a higher density than that inside the porous material (inside raw material).

4. Evaluation on Degradation Ability to Organic Contaminant [FIGS. 8 to 11]:

Assuming a method of decontaminating contaminated water by passing the contaminated water through a support for holding a complexed accumulation of degrading bacteria, the degradation ability of the support for holding a complexed accumulation of degrading bacteria for various kinds of organic contaminant was evaluated as follows. At first, a reflux device 1 shown in FIG. 2 was prepared. Then, the reflux device 1 was filled with 6.25 g of the support for holding a complexed accumulation of degrading bacteria (corresponding to 2.5 g of the dried product). Subsequently, 150 ml of an inorganic salt medium containing 5 ppm of simazine, 5 ppm of atrazine, 2.5 ppm of PCP, and 2.5 ppm of HCB was used as a reflux solution and then refluxed through the support for holding a complexed accumulation of degrading bacteria. The reflux solution was replaced with new one every one week. The reflux was carried out for three weeks in total. The degradation ability of the support for holding a complexed accumulation of degrading bacteria to various kinds of organic contaminant was evaluated by measuring the concentrations of various organic contaminants and the chlorine ion concentration in the reflux solution.

Figure 8:
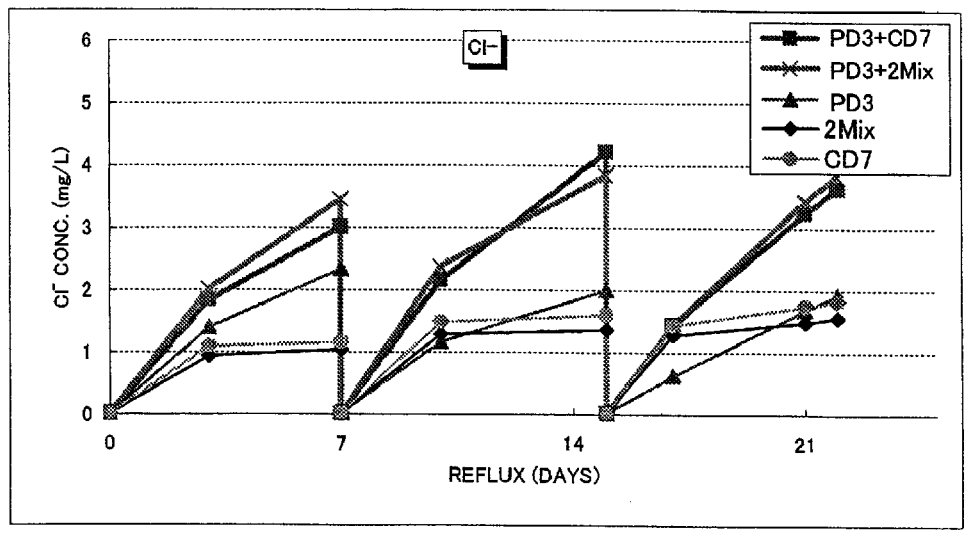
FIG. 8 is a graphical representation of the relationship between the number of reflux days and the concentration of chloride ion when an organic contaminant is refluxed through the support for holding a complexed accumulation of degrading bacteria.
Figure 9:
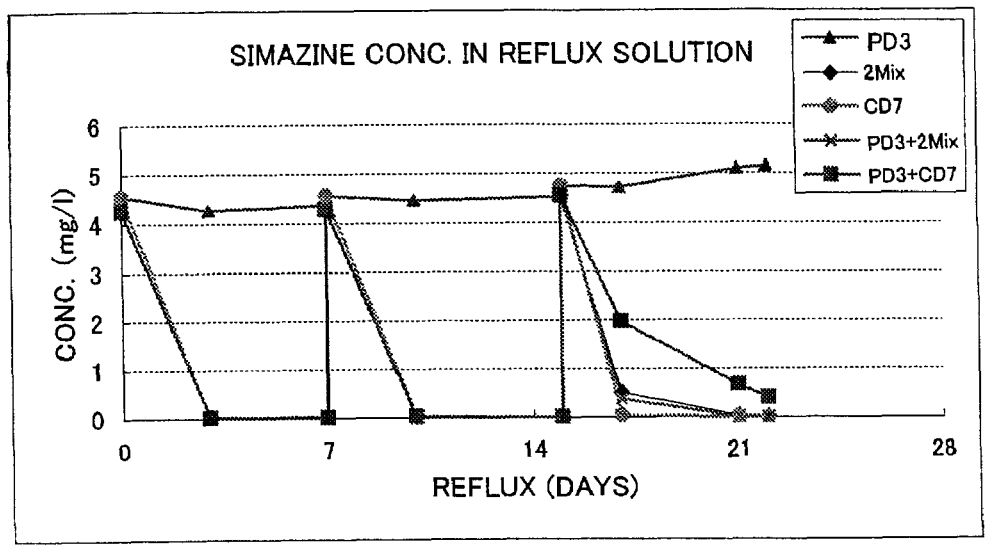
FIG. 9 is a graphical representation of the relationship between the number of reflux days and the concentration of simazine when an organic contaminant is refluxed through the support for holding a complexed accumulation of degrading bacteria.
Figure 10:
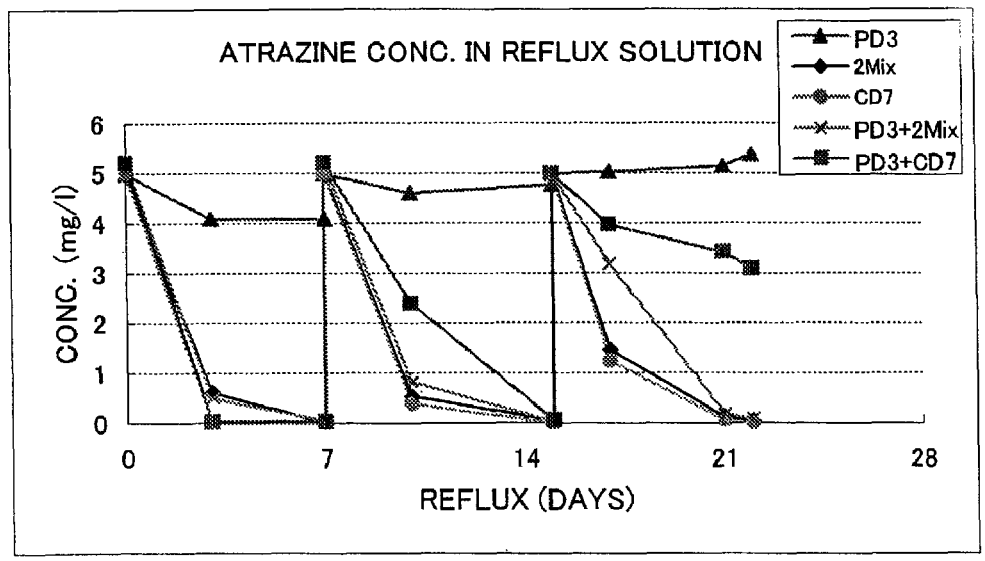
FIG. 10 is a graphical representation of the relationship between the number of reflux days and the concentration of atrazine when an organic contaminant is refluxed through the support for holding a complexed accumulation of degrading bacteria.
Figure 11:
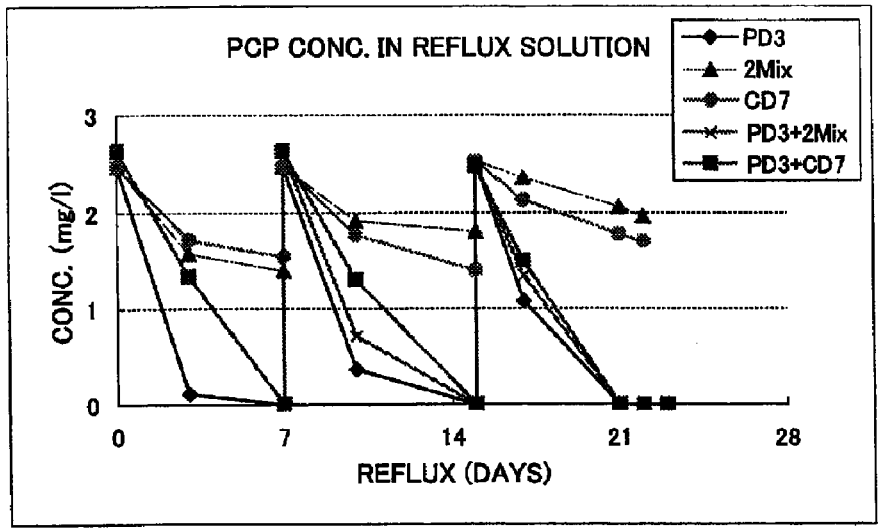
FIG. 11 is a graphical representation of the relationship between the number of reflux days and the concentration of PCP when an organic contaminant is refluxed through the support for holding a complexed accumulation of degrading bacteria.

The relationship between the number of reflux days and the chlorine ion concentration is shown in FIG. 8. In addition, the relationship between the number of reflux days and each of the simazine concentration, atrazine concentration, and PCP concentration is shown in each of FIGS. 9 to 11.

In the support for holding a complexed accumulation of degrading bacteria, which contained a complex system of PD3, CD7, and 2Mix, simazine, atrazine, and PCP were decomposed because of a decrease in concentration of each of organic contaminants. By the way, HCB was adsorbed on the sintered glass filter 2 used in the reflux device 1, so that the degradation ability cannot be evaluated sufficiently. In this case, however, it is found that the support may bear at least degradation ability.

From a decrease in concentration of each kind of organic contaminant, comparing with the single fraction, it is found that the number of degrading bacterial cells in the porous material can be decreased to about $\frac{1}{100}$ to $\frac{1}{10}$ in the case of the support for holding a complexed accumulation of degrading bacteria. However, from the results of decomposing various organic contaminants, the degradation ability to the organic contaminant is sufficient. In particular, the support for holding a complexed accumulation of degrading bacteria, on which PD3 and CFD7 are held (hereinafter referred to as "PD3/CD7-holding support" and the support for holding a complexed accumulation of degrading bacteria, on which PD3 and 2Mix are held (hereinafter, referred to as a PD3/2Mix-holding support) decompose PCNB and simazine 90% or more, respectively. In addition, atrazine and PCP, which are organic contaminants other than PCNB and simazine, can be decomposed 90% or more.

Furthermore, when the PD3/2Mix-holding support is compared with the PD3/CD7-holding support, from the difference between the amounts of chlorine ions generated, it is found that the PD3/CD7-holding support can accumulate the degrading bacteria at a higher density than that of the PD3/2Mix-holding support.

Figure 12:
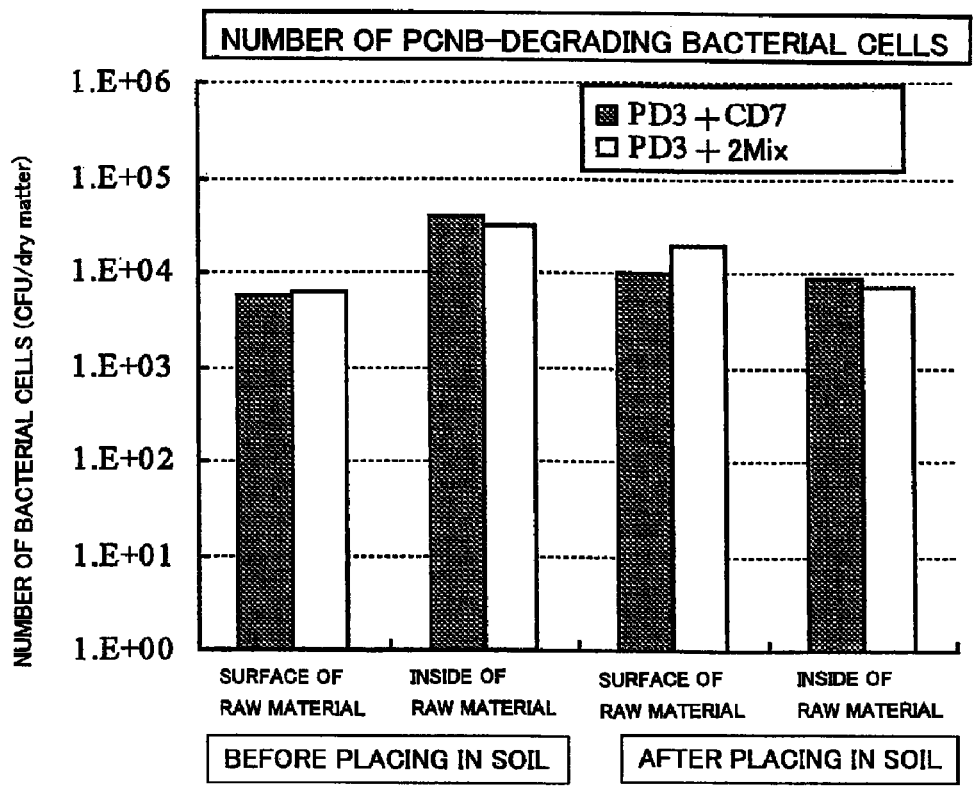
FIG. 12 is a graphical representation of the number of bacterial cells of the PCNB-degrading bacterium before and after a test of decomposing organic contaminants.
Figure 13:
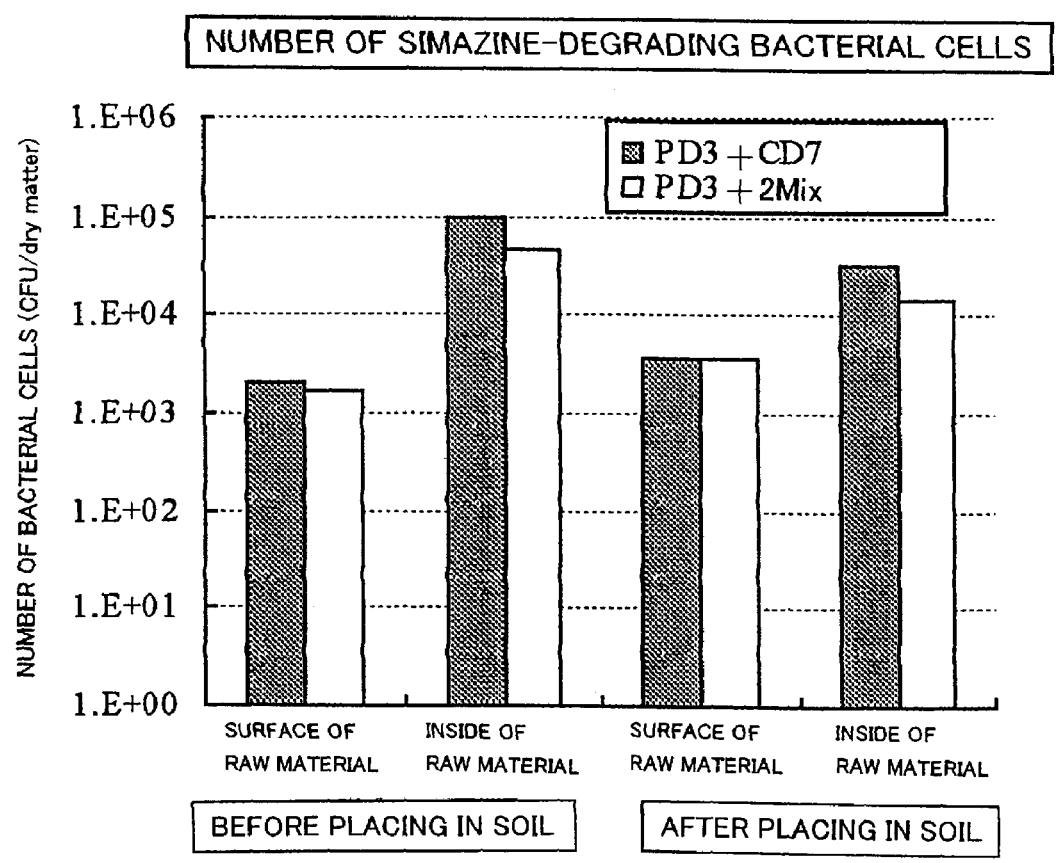
FIG. 13 is a graphical representation of the number of bacterial cells of the simazine-degrading bacterium before and after a test of decomposing organic contaminants.

5. Evaluation on the Degradation Ability to Organic Contaminant (2) [Table 1, FIGS. 12 and 13]

Assuming a method of decontaminating contaminated soil by mixing a support for holding a complexed accumulation of degrading bacteria in the soil, the degradation ability of the support for holding a complexed accumulation of degrading bacteria for various kinds of organic contaminant was evaluated separately from the above item (1) as follows. 80 g of plantation soil (soil texture: L, pH: 6.2, T-C: 0.9%, corresponding dried soil: 59.6 g) mixed with simazine (SI): 5 ppm, atrazine (AT): 5 ppm, PCP: 5 ppm, and HCB: 5 ppm was mixed with 15 g of a support for holding a complexed accumulation of degrading bacteria (corresponding to 6.0 g of dried product) and then filled into a column (5φ×7.5 cm). Subsequently, the column was allowed to stand for 4 weeks at 25° C. During such a period, the column was watered with 15 to 30 ml of water once per week and percolating water was then collected, followed by determining the concentration of each drug. Furthermore, the concentration of each of the drugs in the soil and the support for holding a completed accumulation of degrading bacteria obtained after 4 weeks (after terminating the test) and the number of bacterial cells of each of the degrading bacteria on the surface of, and inside, the support for holding a completed accumulation of degrading bacteria were determined by the MPN method in the same way as that of the method described above, respectively. The results are listed in Table 1 and shown in FIGS. 12 and 13.

TABLE 1

Remaining amounts and degradation rates of various drugs in soil, carbonized ligneous material A, and percolating water after terminating the column test

| | Remaining amount (mg) | Control plot | | | | PD3←CD7 | | | | PD3 + 2Mix | | | |
|---|---|---|---|---|---|---|---|---|---|---|---|---|---|
| | | SI | AT | PCP | HCB | SI | AT | PCP | HCB | SI | AT | PCP | HCB |
| Soil Material A | In dried soil | 0.078 | 0.098 | 0.075 | 0.149 | 0.058 | 0.064 | 0.059 | 0.135 | 0.061 | 0.065 | 0.062 | 0.138 |
| Percolating water | In dried product | 0.198 | 0.181 | 0.205 | 0.135 | 0.002 | 0.002 | 0.002 | 0.003 | 0.002 | 0.003 | 0.002 | 0.003 |
| | Remaining amount in total | 0.021 | 0.019 | 0.017 | 0.013 | 0.010 | 0.011 | 0.012 | 0.008 | 0.011 | 0.012 | 0.013 | 0.009 |
| | Whole remaining amount | 0.2974 | 0.2974 | 0.2967 | 0.2974 | 0.071 | 0.078 | 0.073 | 0.145 | 0.075 | 0.079 | 0.077 | 0.150 |
| | Degradation rate (%) | 0.2 | 0.2 | 0.4 | 0.2 | 76.2 | 73.9 | 75.5 | 51.2 | 74.9 | 73.5 | 74.1 | 49.6 |

Remark: Carbonized ligneous material A without accumulation of degrading bacteria is used as a control
Input amount of each drug into soil: 0.298 mg As is evident from Table 1, the support for holding a complexed accumulation of degrading bacteria (PD3 and CD7) and the support for holding a complexed accumulation of degrading bacteria (PD3 and 2Mix) showed extremely high degradation and removal abilities of about 75% in soil with respect to simazine, atrazine, and PCP but the abilities decreased to about 50% with respect to HCB. This is probably because the aqueous solubility of HCB is 0.005 ppm, which is extremely lower than that of any other drug, and thus the amount of HCB adsorbed in the porous material with the translocation/diffusion of water decreases by about 35% (see the control plot). In addition, from FIGS. 12 and 13, it is found that each of the PCNB-degrading bacterium PD3 and the simazine-degrading bacterium CD7 is accumulated at a high density without a substantial change in the number of bacterial cells before and after placing in the soil. In addition, it is found that degrading bacterial cells are accumulated at a higher density inside the porous material (inside raw material) than that on the surface of the porous material (the surface of the raw material). Furthermore, the total number of bacterial cells inside the porous material in which CD7 including CD7w is accumulated is larger than that of the porous material in which 2Mix free of CD7w is accumulated. It is found that CD7w may enhance the accumulation of bacterial cells inside the porous material.

Figure 14:
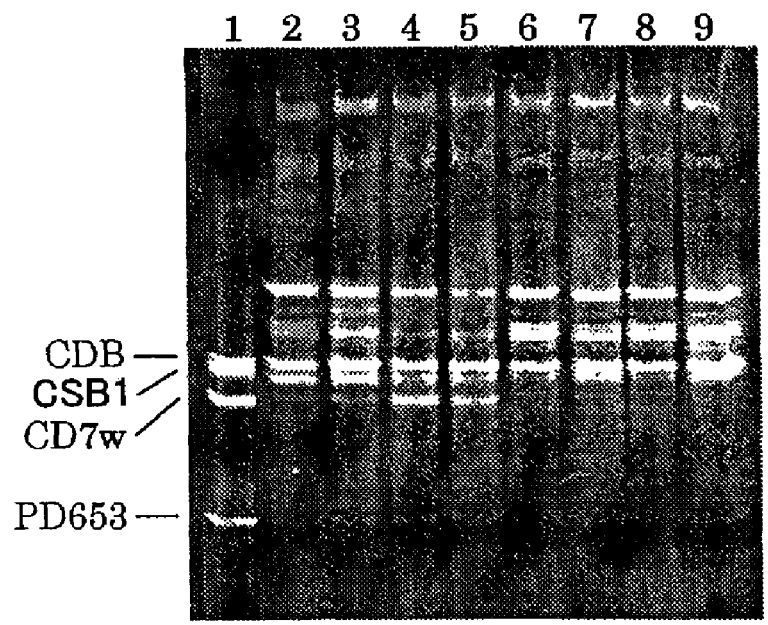
FIG. 14 is a diagram that represents the constituent bacteria in the support for holding a complexed accumulation of degrading bacteria by PCR-DGGE.

6. Accumulation of Degrading Bacterium in Porous Material [FIG. 14]:

Before and after mixing with soil, a $10^1$-fold dilute solution with a phosphate buffer was prepared from each of various supports for holding a complexed accumulation of degrading bacteria by the same method as one described above, and then bacterial cells and the porous material were collected by centrifugation. A sample of the surface of the porous material used was FastDNA kit (Qbiogene, Co., Ltd.) and a sample of the inside of the porous material (about 0.3 g) used was added with 125 µl of SuperBlock (PIERCE, Co., Ltd.) to extract DNA using FastDNA kit for SOIL (Obiogene, Co., Ltd.). The extracted DNA was subjected to PCR-DGGE with a Muyzer method to investigate and analyze the accumulation and transition of a degrading bacterium to the porous material.

As shown in Table 14, the PCR-DGGE confirmed the accumulation of: PD653 constituting the PCNB-degrading bacterium PD3; and CDB21, CSB1, and CD7w constituting the simazine-degrading bacterium CD7 on the porous material. The amount of PD653 may be sufficient for the degradation of PCNB in spite of a small abundance ratio of PD653. It is found that almost no CD7w is present on the surface of the porous material but highly accumulated inside the porous material. Therefore, the compatibility of the bacterial group to the porous material may be enhanced. There is no change in the configuration of a bacterial group accumulated before and after mixing the support for holding a complexed accumulation of degrading bacteria in soil. In addition, neither adhesion nor inversion of a soil bacterium into the porous material was observed.

What is claimed is:

1. A method of decontaminating a polluted environment, comprising embedding a support in said polluted environment for a time and in such a manner to decontaminate said environment,
wherein said support comprises a porous material and a bacteria selected from the group consisting of PD3 and PD653;
wherein said PD3 is a mixture of bacteria comprising *Nocardioides* sp. PD653 and *Burkholderia cepacia* KTYY97;
wherein said bacteria is capable of degrading at least one organic contaminant selected from the group consisting of PCNB, PCP and HCB; and
wherein said bacteria is enriched on the porous material.

2. The method of decontaminating a polluted environment of claim 1, wherein said environment is polluted by PCNB, and said organic contaminant is PCNB.

3. The method of decontaminating a polluted environment of claim 1, wherein said environment is polluted by PCP, and said organic contaminant is PCP.

4. The method of decontaminating a polluted environment of claim 1, wherein said environment is polluted by HCB, and said organic contaminant is HCB.

5. A method of decontaminating a polluted environment according to claim 1,
wherein said polluted environment comprises contaminated water or soil; and
wherein said degrading comprises decomposing the organic contaminant in the contaminated water or soil.

6. A method of decontaminating a polluted environment according to claim 1, further comprising mixing the support in said polluted environment, wherein said polluted environment comprises contaminated water or soil.

7. A method of decontaminating a polluted environment according to claim 6, wherein said organic contaminant is PCNB.

8. A method of decontaminating a polluted environment according to claim 6, wherein said organic contaminant is PCP.

9. A method of decontaminating a polluted environment according to claim 6, wherein said organic contaminant is HCB.

10. A method of decontaminating a polluted environment according to claim 5, wherein said organic contaminant is PCNB.

11. A method of decontaminating a polluted environment according to claim 5, wherein said organic contaminant is PCP.

12. A method of decontaminating a polluted environment according to claim 5, wherein said organic contaminant is HCB.

* * * * *

UNITED STATES PATENT AND TRADEMARK OFFICE
CERTIFICATE OF CORRECTION

PATENT NO.       : 8,283,154 B2                                             Page 1 of 1
APPLICATION NO.  : 12/561078
DATED            : October 9, 2012
INVENTOR(S)      : Takagi et al.

It is certified that error appears in the above-identified patent and that said Letters Patent is hereby corrected as shown below:

Section (30) on the title page, line 1 should be amended as follows:
2005-018901

Signed and Sealed this
Twenty-second Day of January, 2013

David J. Kappos
*Director of the United States Patent and Trademark Office*

SEQUENCE LISTING

<160> NUMBER OF SEQ ID NOS: 2

<210> SEQ ID NO 1
<211> LENGTH: 1487
<212> TYPE: DNA
<213> ORGANISM: Nocardioides sp. PD653

<400> SEQUENCE: 1
gacgaacgct ggcggcgtgc ttaacacatg caagtcgagc ggtaaggccc tttcgggggt      60
acacgagcgg cgaacgggtg agtaacacgt gagtaatctg cccttcactt ggggataagc     120

```
accggaaacg gtgtctaata cccgatacga ccaacccctg catggggtgt tggtggaaag    180
ttttttcggt gggggatgtg ctcgcggcct atcagcttgt tggtggggta atggcctacc    240
aaggcttcga cgggtagccg gcctgagagg gtgaccggcc acactgggac tgagacacgg    300
cccagactcc tacgggaggc agcagtgggg aatattggac aatgggcgga agcctgatcc    360
agcaacgccg cgtgagggat gacggccttc gggttgtaaa cctctttcag cggggacgaa    420
gcgccgatga tggtggtgac ggtacccgca gaagaagcac cggccaacta cgtgccagca    480
gccgcggtaa tacgtagggt gcgagcgttg tccggaatta ttgggcgtaa agggctcgta    540
ggcggtttgt cgcgtcggga gtgaaaacac cgggcttaac tcggtgcttg ctttcgatac    600
gggcagacta gaggtatgca ggggagaacg gaattcctgg tgtagcggtg aaatgcgcag    660
atatcaggag gaacaccggt ggcgaaggcg ttctctggg cattacctga cgctgaggag    720
cgaaagtgtg gggagcgaac aggattagat accctggtag tccacaccgt aaacgttggg    780
cgctaggtgt ggggcctatt ccatgggttc cgtgccgcag ctaacgcatt aagcgccccg    840
cctggggagt acggccgcaa ggctaaaact caaaggaatt gacggggggcc cgcacaagcg    900
gcggagcatg cggattaatt cgatgcaacg cgaagaacct tacctgggtt tgacatatgc    960
cggaaagccc cagagatggg gcccctttta gtcggtatac aggtggtgca tggctgtcgt   1020
cagctcgtgt cgtgagatgt tgggttaagt cccgcaacga gcgcaaccct cgtcctatgt   1080
tgccagcatg ccttcgggtg atgggactc ataggagact gccggggtca actcggagga   1140
aggtggggat gacgtcaagt catcatgccc cttatgtcca gggcttcacg catgctacaa   1200
tggccggtac aaagggctgc gatgctgtaa ggcggagcga atcccaaaaa gccggtctca   1260
gttcggattg gggtctgcaa ctcgacccca tgaagtcgga gtcgctagta atcgcagatc   1320
agcaacgctg cggtgaatac gttcccgggc cttgtacaca ccgcccgtca cgtcacgaaa   1380
gtcggcaaca cccgaagccg gtggcctaac ccttgtggag ggagccgtcg aaggtggggc   1440
tggcgattgg gacgaagtcg taacaaggta gccgtaccgg aagtgc              1487
```

<210> SEQ ID NO 2
<211> LENGTH: 831
<212> TYPE: DNA
<213> ORGANISM: Arthrobacter sp. CD7w

<400> SEQUENCE: 2

```
atattgcaca atgggcggaa gcctgatgca gcgacgccgc gtgagggatg acggccttcg     60
ggttgtaaac ctctttcagt agggaagaag cgtaagtgac ggtacctgca gaagaagcgc    120
cggctaacta cgtgccagca gccgcggtaa tacgtagggc gcaagcgtta tccggaatta    180
ttgggcgtaa agagctcgta ggcggttttgt cgcgtctgcc gtgaaagtcc ggggctcaac    240
tccggatctg cggtgggtac gggcagacta gagtgatgta ggggagactg gaattcctgg    300
tgtagcggtg aaatgcgcag atatcaggag gaacaccgat ggcgaaggca ggtctctggg    360
cattaactga cgctgaggag cgaaagcatg gggagcgaac aggattagat accctggtag    420
tccatgccgt aaacgttggg cactaggtgt ggggacatt ccacgttttc cgcgccgtag    480
ctaacgcatt aagtgccccg cctggggagt acggccgcaa ggctaaaact caaaggaatt    540
gacggggggcc cgcacaagcg gcggagcatg cggattaatt cgatgcaacg cgaagaacct    600
taccaaggct tgacatgaac cggaaacgcc tggaaacagg tgccccactt gtggtcggtt    660
```

-continued

```
tacaggtggt gcatggttgt cgtcagctcg tgtcgtgaga tgttgggtta agtcccgcaa    720
cgagcgcaac cctcgttcta tgttgccagc acgtgatggt ggggactcat aggagactgc    780
cggggtcaac tcggaggaag gtggggacga cgtcaaatca tcatgcccct t             831
```